United States Patent [19]
Stoop et al.

[11] Patent Number: 5,954,754
[45] Date of Patent: Sep. 21, 1999

[54] SINGLE PASS LEAD DUAL CHAMBER PACING SYSTEM WITH MEANS FOR EVALUATING EFFICIENCY OF ATRIAL PACING

[75] Inventors: Gustaaf A.P. Stoop, Dieren; Geeske van Oort, Nieuwleusen, both of Netherlands

[73] Assignee: Vitatron Medical, B.V., Dieren, Netherlands

[21] Appl. No.: 08/850,471

[22] Filed: May 5, 1997

[51] Int. Cl.⁶ ........................................... A61N 1/37
[52] U.S. Cl. ............................................... 607/28
[58] Field of Search .................................. 607/28

[56] References Cited

U.S. PATENT DOCUMENTS

| | | | |
|---|---|---|---|
| 4,917,115 | 4/1990 | Flammang et al. | 128/419 PG |
| 5,078,133 | 1/1992 | Heinz et al. | 128/419 PG |
| 5,103,820 | 4/1992 | Markowitz | 128/419 OPG |
| 5,129,393 | 7/1992 | Brumwell | 128/419 PG |
| 5,170,785 | 12/1992 | Heinz et al. | 128/419 PG |
| 5,172,694 | 12/1992 | Flammang et al. | 128/642 |
| 5,190,052 | 3/1993 | Schroeppel | 128/786 |
| 5,237,992 | 8/1993 | Poore | 607/18 |
| 5,247,929 | 9/1993 | Stoop et al. | 607/14 |
| 5,247,930 | 9/1993 | Begemann et al. | 607/11 |
| 5,312,445 | 5/1994 | Nappholz et al. | 607/9 |
| 5,324,327 | 6/1994 | Cohen | 607/122 |
| 5,391,189 | 2/1995 | van Krieken et al. | 607/17 |
| 5,411,533 | 5/1995 | Dubreuil et al. | 607/28 |
| 5,454,836 | 10/1995 | van der Veen et al. | 607/9 |
| 5,458,623 | 10/1995 | Lu et al. | 607/28 |
| 5,531,771 | 7/1996 | van der Veen | 607/9 |
| 5,549,648 | 8/1996 | Stoop | 607/9 |
| 5,571,144 | 11/1996 | Schroeppel | 607/28 |
| 5,628,778 | 5/1997 | Kruse et al. | |

FOREIGN PATENT DOCUMENTS

| | | |
|---|---|---|
| WO96/15665 | 5/1996 | WIPO . |
| WO/96/25977 | 8/1996 | WIPO . |

*Primary Examiner*—William E. Kamm
*Attorney, Agent, or Firm*—Woodcock Washburn Kurtz Mackiewicz & Norris, LLP

[57] ABSTRACT

There is provided a pacing system, preferably a VDD system having a single pass lead with one or two ventricular electrodes and a pair of atrial electrodes. The pacemaker has timing and logic capability for determining when an atrial back-up pulse, such an atrial synchronization pulse, can be delivered, and also whether the pacemaker can provide for continuing atrial pacing. The pacemaker is provided with a plurality of modules for determining the likelihood that a delivered atrial pace pulse resulted in atrial contraction, and for storing data relating to the probable capture or no_capture result of each delivered pace pulse. One of the capture-determining modules is a timing module which stores a plurality of rules by which a sequence of events and rates surrounding a delivered atrial pace pulse is analyzed to determine the probability of capture. The pacemaker carries out capture probability determinations following each delivered pace pulse, and on the basis of such continuous determinations evaluates atrial pace pulse capture efficiency, and adjusts the atrial pace pulse output level to optimize atrial pacing.

21 Claims, 11 Drawing Sheets

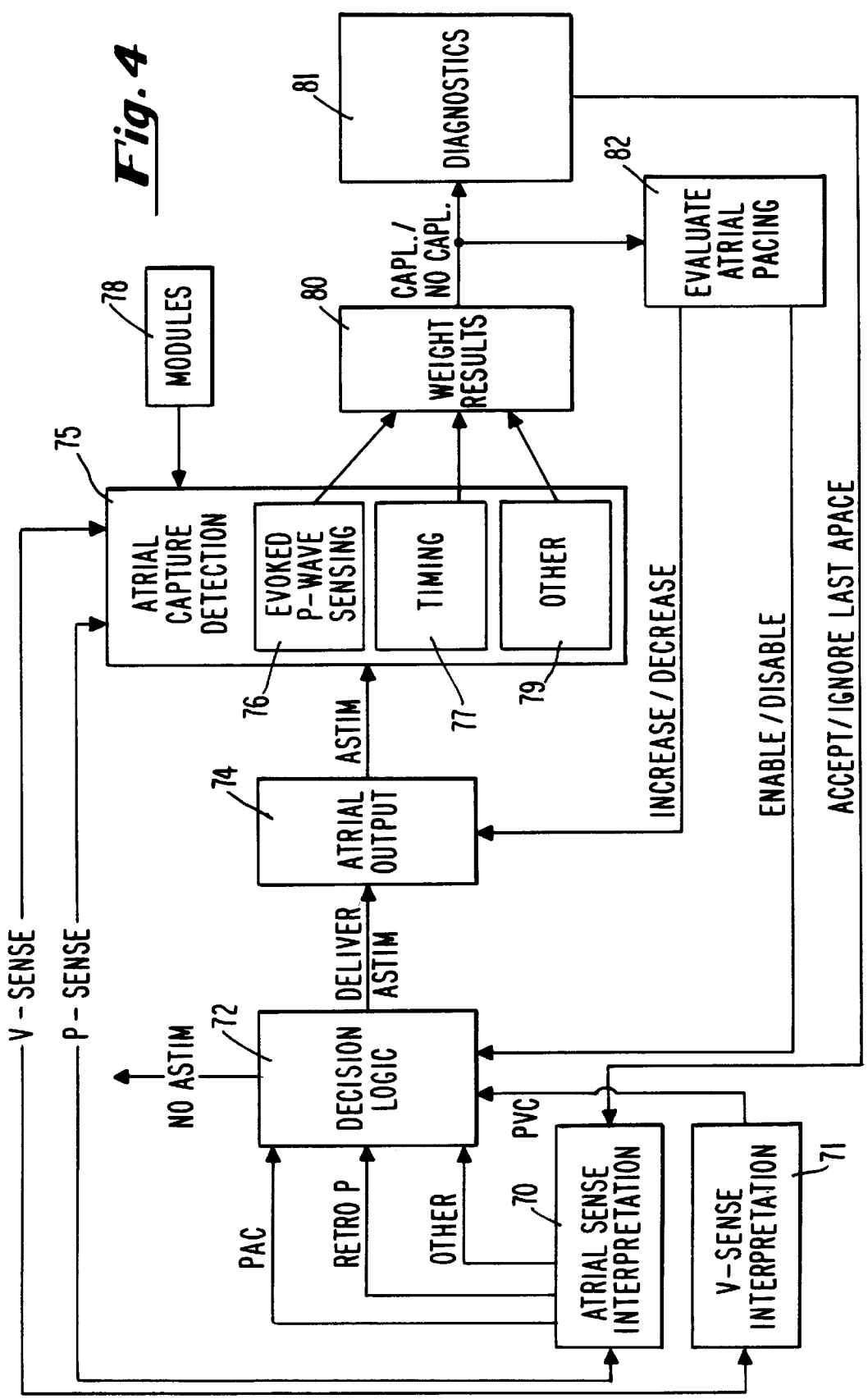

SINGLE PASS LEAD DUAL CHAMBER PACING SYSTEM WITH MEANS FOR EVALUATING EFFICIENCY OF ATRIAL PACING

FIELD OF THE INVENTION

This invention relates to dual chamber pacing systems and, more particularly, single pass lead dual chamber pacing systems having the capability of atrial pacing.

BACKGROUND OF THE INVENTION

A dual chamber pacing system offers the significant advantage of providing AV-synchrony when the atrial rate can be tracked, i.e., is physiologic. Thus, every time an atrial beat is sensed at a physiological rate, the pacemaker delivers a synchronized ventricular pace pulse in the absence of a timely natural ventricular beat. Such a pacemaker system generally has some form of upper tracking limit, such as a dynamic tracking limit disclosed in U.S. Pat. Nos. 5,531,771 and 5,549,648, assigned to the same assignee as this invention, and incorporated herein by reference. Whenever the P-wave is sensed at a rate below the tracking limit, the synchronous ventricular pace pulse is prepared by timing out an appropriate AV interval following the occurrence of the P-wave. For a sensed P-wave at a higher rate, pacemaker may provide for Wenckebach operation, but generally higher rate non-physiological atrial signals are not tracked. AV synchrony can also be lost due to other circumstances, such as the sensing of a PVC or a pacemaker determination of ongoing retrograde conduction. Since AV synchrony is highly desirable, pacemaker systems attempt to re-establish such synchronous operation as soon as possible after a loss of tracking. One technique for doing this, which is disclosed in the above referenced patent, is the delivery of an atrial synchronization pulse (ASP), which is used in DDD systems having atrial and ventricular leads.

The problem of re-establishing AV synchrony after loss of tracking is more acute in a VDD pacing system having a single pass lead. As is known, the single pass lead has one or two electrodes to pace and sense in the ventricle, and a pair of floating ring electrodes positioned on the lead so that they are placed in the atrium where they sense P-waves.

While a VDD pacing system is designed to pace only in the ventricle, it has been observed in patients that pacing through the atrial rings in a single pass lead VDD system may also provoke atrial contraction. However, because the rings are floating in the atrium, the stimuli may not be effective. In the extreme, where these rings are positioned far from the atrial wall, no atrial pacing may be possible; where the rings are fortuitously placed closer to the atrial wall, most of the delivered atrial pace stimulus pulses may be effective. Whether or not atrial pacing is reliable in such a single pass lead system either for occasional delivery of ASPs or more generally for ongoing constant atrial pacing, is a circumstance that will vary from patient to patient. Likewise, a dual pacing system with an atrial lead as well as a ventricular lead may not have 100% atrial pacing efficiency, due to atrial lead dislodgement, or too high chronic atrial pacing threshold.

Accordingly, an objective of this invention is to provide a pacemaker having an algorithm particularly applicable to single pass VDD lead systems for determining when an atrial pace should be delivered; providing pacing through the atrial electrodes; and evaluating whether or not the pace was effective. Through such ongoing evaluation over a number of atrial paces, the pacemaker system can adjust the atrial pace pulse output level either lower or higher, or may even disable atrial pacing if the efficiency is too low. If pacing efficiency is high enough, the pacemaker can operate in the DDD mode. The invention further aims to provide diagnostic counters for an indication of the atrial pacing effectiveness, so that the physician, through an external programmer, can determine a desired pacing mode.

SUMMARY OF THE INVENTION

It is an object of this invention to provide a pacing system, particularly one which utilizes a single pass lead with floating atrial electrodes, which has the capability of evaluating the efficiency by which atrial pace pulses delivered through the floating atrial electrodes result in capture of the atrium. It is a further object of this invention to obtain data relating to atrial capture efficiency, and to utilize such data to control the output of atrial paces and/or the circumstances when atrial pacing is enabled, to optimize atrial pacing when the lowest amount of energy expenditure.

In accordance with the above objects, there is provided a preferred embodiment pacing system for dual mode pacing, having a single pass lead for delivering pace pulses and sensing patient heartbeat signals, the lead having at least one ventricular electrode positioned for placement in the patient's ventricle and a pair of floating atrial electrodes positioned to be in the patient's atrium. The pacemaker has a controllable atrial pace generator for generating and delivering atrial pace pulses through the floating atrial electrodes, and atrial pace control for controlling the timing and circumstances of delivering atrial pace pulses. The system is further characterized by accumulating data relating to the probability that each delivered atrial pace pulse has resulted in atrial capture, and making a determination of the ongoing atrial capture efficiency as a function of atrial pace pulse output level. The atrial pacing is evaluated based on accumulated capture efficiency data, and the atrial pace pulse output level is adjustable as a function of such efficiency determination. While the preferred embodiment is that of a system with a single pass lead, it is also applicable to any pacing system where no reliable information concerning atrial capture, or evoked response, is available.

In a preferred embodiment, the timing of events in relation to given sequences around a delivered atrial stimulus, and particularly an atrial sync pulse, is analyzed, and a determination of the probability of atrial capture is made on the basis of such timing. The pacemaker has a plurality of stored rules applicable for different sequences relating to delivering an ASP, for determining the probability that there was or was not a capture. Such probabilities are weighted depending upon the detected pattern, and when a sufficient amount of probability data has been accumulated, the atrial pacing efficiency is evaluated. The output level of atrial pace pulses is adjusted to the lowest level consistent with an acceptably high percentage of atrial capture.

BRIEF DESCRIPTION OF THE DRAWINGS

FIG. 4 is a system block diagram showing the functional components of a pacing system in accordance with this invention.

DESCRIPTION OF THE PREFERRED EMBODIMENTS

Figure 1:
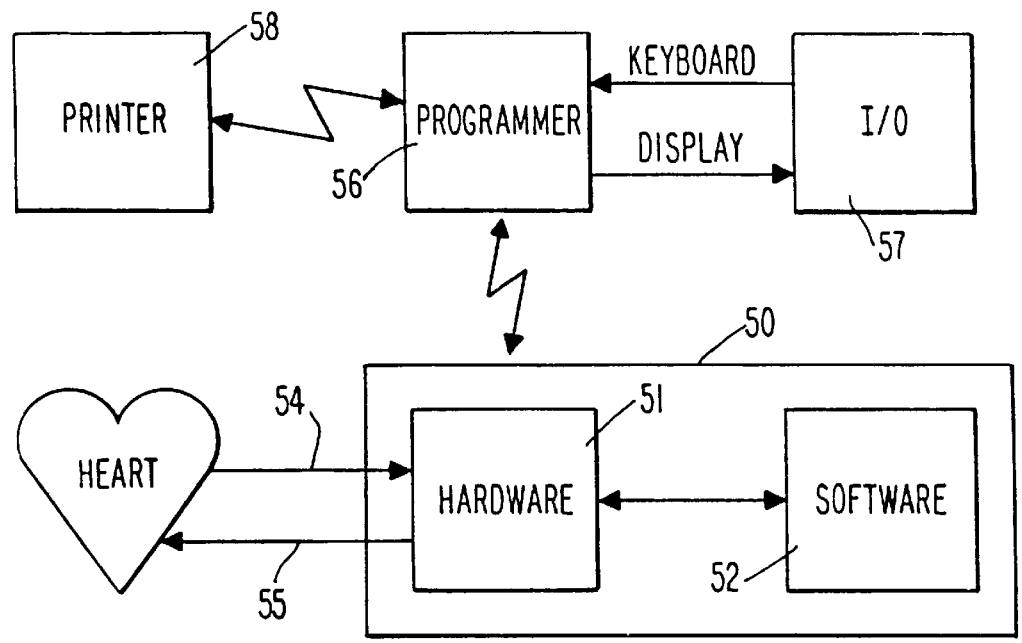
FIG. 1 is a block diagram of the overall system of the invention, showing the environment in which the pacemaker operates.

The pacing system of this invention is preferably software-based, i.e., the software controls functions through hardware, as illustrated in FIG. 1. Referring specifically to FIG. 1, the pacemaker 50 is shown as having a component hardware portion 51 and a software portion 52, the two portions being interconnected. The software is parameter-driven, i.e., there are numerous parameters that control the pacing behavior, diagnostic functions, etc. The hardware is interconnected with the patient's heart by one or more electrodes 55, and one or more sensor connections 54. As is well understood in the art, for a dual chamber pacemaker, there are generally two leads, an atrial lead and a ventricular lead, each lead having at least one electrode, unipole or bipole, positioned in the heart. As discussed further below, for a VDD pacing system, a single pass lead is used, which serves to sense in the atrium, and to sense and pace in the ventricle. The line 54 is illustrated as leading from the heart, as in a QT-type sensor arrangement, but may be attached to the outside case of the pacemaker or may couple to any other available sensors for sensing body parameter information used in rate responsive pacing systems.

As further illustrated in FIG. 1, the pacer 50 is in telemetric communication with a programmer 56. The user can select parameters and program them through programmer 56, and can also interrogate parameter and diagnostic data from the implanted pacemaker. Interrogated information from the pacer can be coupled by telemetry directly to a printer 58. Input/output devices 57 are used to input information by the user to the programmer, or to display information received by the programmer from the pacemaker.

Figure 2:
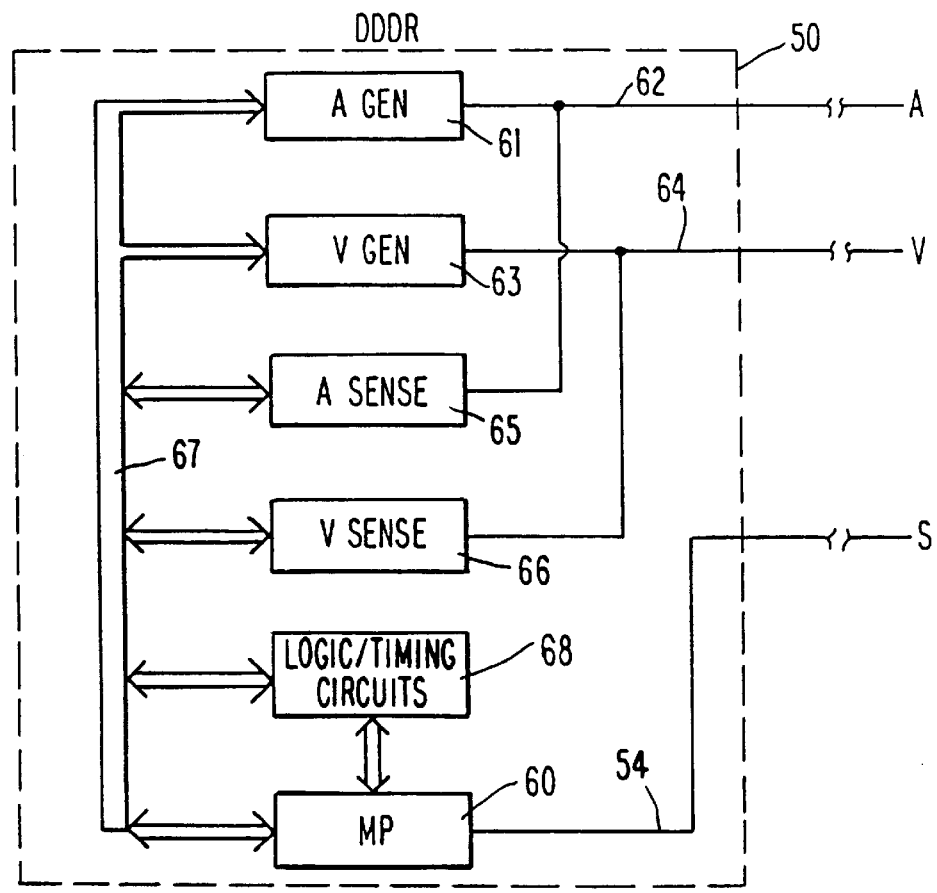
FIG. 2 is a block diagram which illustrates basic components of the pacemaker of this invention, together with a lead for delivering signals to and receiving signals from the patient's heart.

Referring to FIG. 2, there is shown a basic block diagram of the primary components of a VDD or DDD pacer 50. An atrial generator 61 is shown, having an output connected to 62 which communicates through to one or two electrodes in the patient's atrium. An A-sense amplifier 65 is illustrated also connected to atrial lead 62. A ventricular generator 63 is illustrated which is connected to the patient's ventricle through lead 64. The ventricular pace pulses (VP) are connected either to a pair of bipolar electrodes at about the distal tip of the lead, or to a unipolar lead electrode and an indifferent electrode which is suitably on or a part of the pacemaker case. As used herein, delivery of a VP to at least one ventricular tip electrode refers to either unipolar or bipolar operation. V-sense amplifier 66 is also connected to lead 64, to receive and sense signals from the patient's ventricle. For a DDD system, leads 62 and 64 are separate leads; for a VDD system, leads 62 an 64 are common, and the atrial generator and atrial sense amplifier are connected to a pair of ring electrodes that float in the patient's atrium. In a rate-responsive embodiment of this invention which incorporates QT rate control, V-sense block 66 also includes means for picking out and determining the timing of the evoked T wave. Generators 61 and 63 and sense blocks 65 and 66 are interconnected with microprocessor system 60, which microprocessor has software which is parameter-driven to control the operation of the hardware units. Microprocessor system 60 may be interconnected with hardware logic and/or timing circuits 68. As affects the scope of this invention, the degree to which software supplants hardware, or vice versa, is a matter of design choice. Thus, for the many timing functions that are carried out in the pacing system of this invention, it is to be understood that the microprocessor may have built in timing circuits, or suitably may control external hardware timer circuits. Software control of pacing function is well known in the art, such that the following detailed discussions of software routines enable one of ordinary skill in this art area to design a system for carrying out the functions within the scope of the invention. Data inputted from programmer 56 is stored in memory associated with microprocessor.

Still referring to FIG. 2, there is shown a sensor S indicated as providing an input to microprocessor system 60. Sensor S represents one or more sensors for monitoring one or more body parameters to provide an indication of desired pacing rate. The pacemaker of this invention may be rate responsive in the manner as described in the referenced U.S. Pat. No. 5,247,930.

Figure 3A:
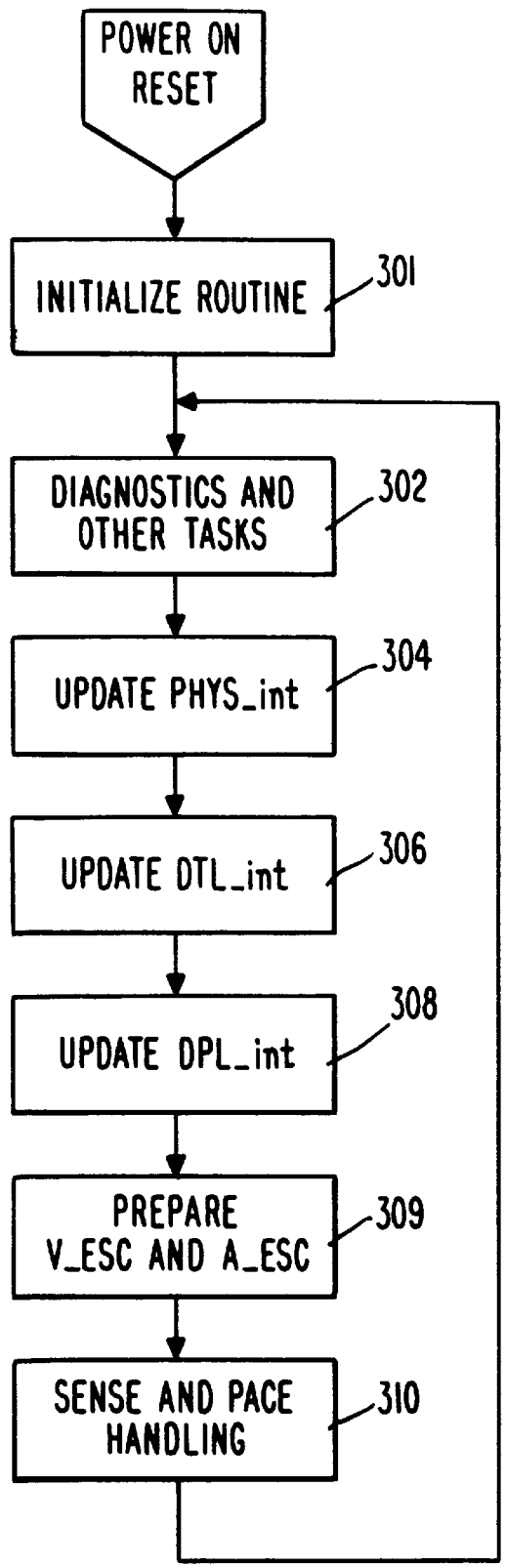
FIG. 3A is a flow diagram showing the main sequential steps carried out each cycle by the pacemaker of this invention.

Referring now to FIG. 3A, there is shown a flow diagram of the main logical steps taken by the pacemaker of this invention. The basic rules of operation are as follows:

For DDD(R) mode, V_Esc=DPL_int and A_Esc=V_Esc−AV_delay.

For VDD(R) mode, V_Esc=DPL_int, and A_Esc is not started. As discussed in the two above-referenced patents, an atrial sync pulse (ASP) can be delivered under certain conditions in order to try to regain synchronous operation. As used herein, an ASP, or an "atrial back-up" pulse is one that is employed in a special situation, e.g., occurrence of a BAS, TAS, WBB, NAB, PVC, PAC or retrograde conduction in order to try to re-establish synchronous pacing. In the context of this invention, the ASP can be used in the VDD as well as the DDD mode of operation.

Entering the routine, the variables are first initialized at 301. At 302, the pacemaker performs any diagnostic or other tests which are programmed. At block 304, the pacemaker updates phys_int which is a measure of the rate of physiological atrial signals, e.g., a running average of the sinus rate so long as it is physiological. Of course, under some conditions there may be no change in phys_int in any given cycle. At block 306, the dynamic tracking limit interval (DTL_int), is updated in coupled relation to phys_int. Likewise, at 308, DPL_int is updated in coupled relation to phys_int. Reference is made to U.S. Pat. No. 5,247,930, which gives a detailed discussion of these decision rates. At block 309, the pacemaker prepares the two escape intervals V_Esc and A_Esc, and waits. As noted above, for a VDD pacing system, A_Esc is not set. Block 310 generally indicates sense and pace handling, i.e., how the pacemaker responds to a sensed event or timeout of one or the other escape intervals.

Figure 3B:
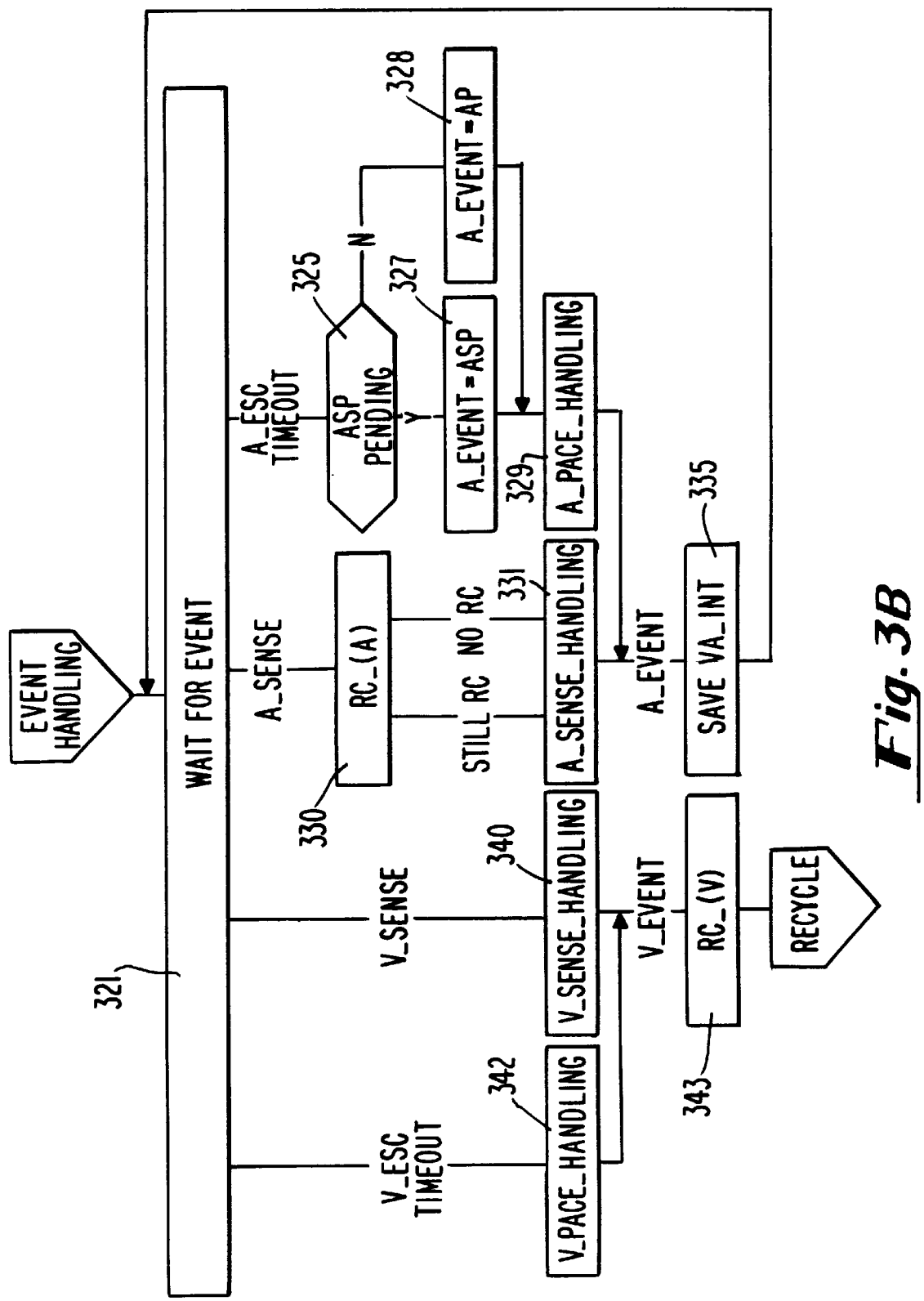
FIG. 3B is a flow diagram of sense and pace handling, indicating how the pacemaker responds to an atrial sense (AS) or ventricular sense (VS), and when it delivers an atrial pace pulse or ventricular pace pulse.

Referring now to FIG. 3B, there is shown a more detailed flow diagram of the sense and pace handling. The routine is entered when no A event has yet occurred during the cycle. At block 321, the pacemaker waits for an event. As indicated, there are four possibilities (handling a T-sense, as in a Q-T pacemaker, is not described). Proceeding from right to left, there can be a timeout of the atrial escape interval, A_Esc, in which case the pacemaker goes to block 325 and determines whether an atrial sync pulse (ASP) is pending. If yes, at 327 the atrial event is stored as an ASP. If no, at block 328 the pacemaker records the event as an AP. The pacemaker then goes to block 329 for A_Pace handling, i.e., delivery of a suitable atrial pace pulse. Returning to block 321, if there is an A-sense, the pacemaker goes to block 330 and carries out the RC_(A) routine, to determine whether there is retrograde conduction (RC). The RC_(A) routine concludes by indicating either "still RC" or "No RC". The pacemaker then proceeds with A-sense handling at block 331, e.g., following through with an appropriate response such as synchronous or asynchronous operation. See U.S. Pat. No. 5,531,771. After A_Sense or A_Pace Handling, at 335 the pacemaker determines and saves VA_int, which is measured from a V event to an A event.

Returning to block 321, the event may be a V-sense, in which case the pacemaker goes to block 340 and handles the response to a V-sense; see U.S. Pat. No. 5,531,771. Or, there can be timeout of the V_Esc, as when the pacemaker is tracking or in the asynchronous mode. In this case the pacemaker goes to block 342 for V_Pace_Handling, i.e., delivers the V-stimulus and records that the V_event was a ventricular pulse (VP). Following either block 340 or 342, the pacemaker goes to 343 and carries out the RC_(V) routine, for determining whether RC is ongoing. See U.S. Pat. No. 5,247,929.

Figure 3C:
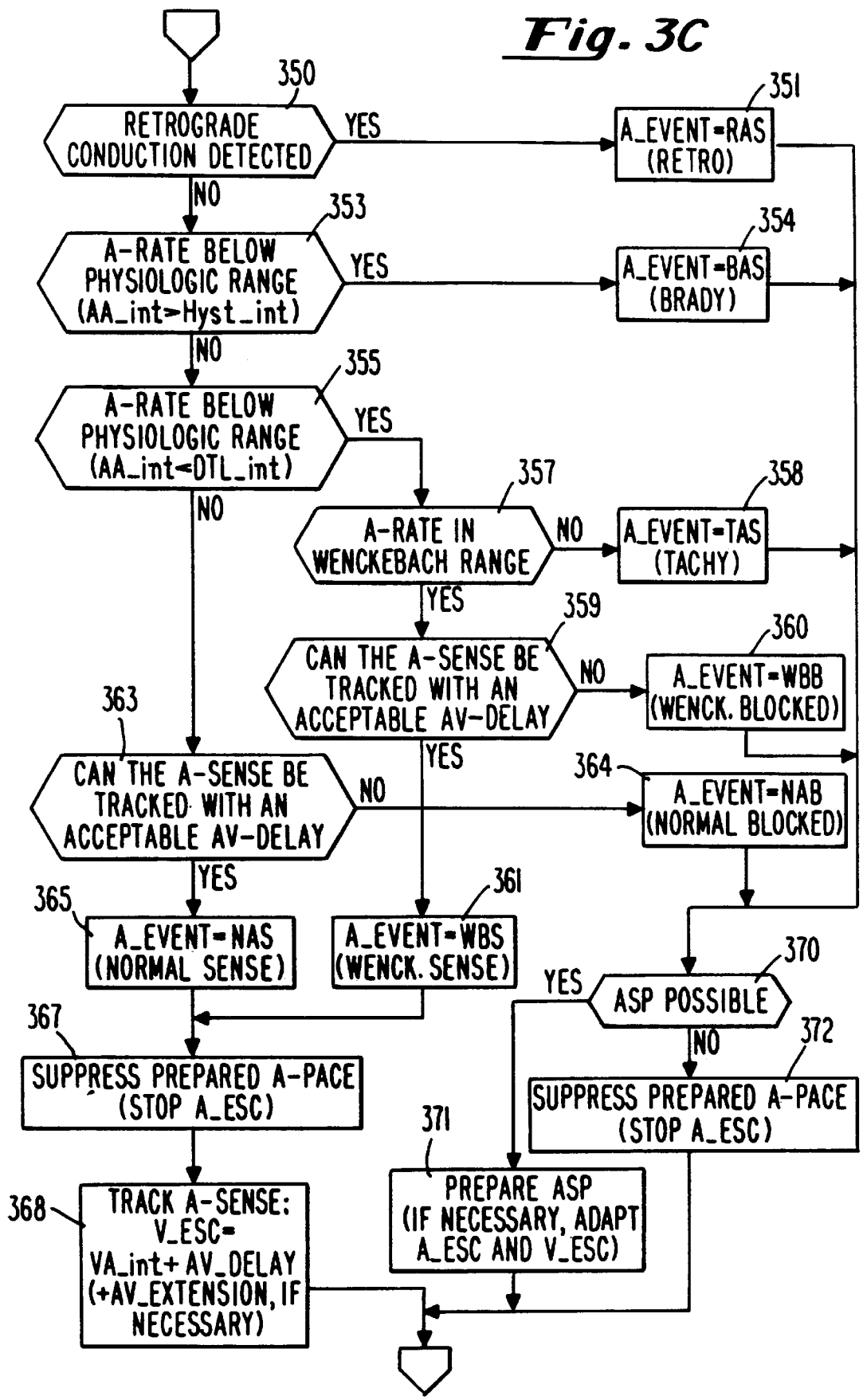
FIG. 3C is a more detailed flow diagram of the subroutine for A-sense handling.

Referring now to FIG. 3C, there is shown a more detailed flow diagram of A-sense handling, or how the pacemaker responds to a sensed atrial signal. At block 350, it is determined whether retrograde conduction has been detected. If yes, the routine branches to block 351, and identifies the event as an RAS, or retro atrial sense. The routine then goes to block 370 and determines whether delivery of an ASP is possible. If yes, the routine goes to block 371 and prepares an ASP, adapting A_Esc and V_Esc as might be required. If no ASP is possible, the prepared A-pace (for DDD operation) is suppressed at block 372, such that no atrial pace is delivered; for VDD operation, step 372 is not necessary.

Returning to block 350, assuming there is no retrograde conduction, the pacemaker goes to block 353 and determines whether the atrial rate is below the physiological range, i.e., whether there has been a brady event. As indicated, this is determined by comparing the AA_int with Hyst_int, where Hyst_int equals DPL_int+A_Hyst, the last factor representing hysteresis below the pacing rate. If the A-rate is below the physiologic range, the pacemaker goes to block 354 and identifies the atrial event as a BAS. As discussed above, the pacemaker may deliver an ASP in case of a BAS, a TAS, a WBB or an NAB, in order to try to resynchronize. However, if it is not below the physiological range, the pacemaker goes to block 355 and determines whether the rate is above the physiological range, i.e., AA_int<DTL_int. If yes, the routine branches to block 357 and determines whether the atrial rate is within the Wenckebach range. If no, at 358 the atrial event is identified as a TAS. However, if the atrial rate is within the Wenckebach range, the routine goes to block 359 and determines whether the A-sense can be tracked with an acceptable AV-delay. If no, the routine goes to block 360 and identifies the atrial event as a WBB, indicating Wenckebach blocked. After a TAS or WBB, the pacemaker proceeds to try to deliver an ASP as shown at block 370. However, if the A-sense can be tracked, the routine goes to block 361 and identifies the atrial event as a WBS, meaning a Wenckebach sense. Thereafter the routines goes to block 367.

Returning to block 355, if the answer is no, this means that the atrial rate is within the physiological range, i.e., between DTL and DPL, taking into account any hysteresis. The routine then goes to block 363 and determines whether the A-sense can be tracked with an acceptable AV delay. If no, meaning that the resulting ventricular pace would be delivered at too high a rate, the pacemaker branches to block 364 and identifies the atrial event as an NAB, i.e., a normal atrial event blocked. After this, it is again determined at 370 whether an ASP is possible, e.g., ASP on NAB. If at 363, the A sense can be tracked, the routine goes to block 365 and identifies the atrial event as NAS, normal atrial sense. Then at block 367 the pacemaker suppresses the prepared atrial pace, and at block 368 the pacemaker tracks the atrial sense, resetting the ventricular escape interval to $VA_{13}$ int+AV_ delay, adding an $AV_{13}$ Extension if necessary.

Referring now to FIG. 4, there is shown a block diagram system overview of the inventive feature of evaluating the efficiency of delivered atrial stimulus pulses, particularly in a single pass lead VDD system. As shown at 70, atrial senses or P senses are inputted into atrial sense interpretation block 70, which carries out the atrial sense interpretation as set forth in FIG. 3C. The possible interpretations of interest here are here PAC; retro P, indicating RC; and other types of P-waves, which are to be used in the following logic. Also, V sense signals are inputted into $V_{13}$ sense interpretation block 71, which provides a PVC indication to decision block 72. Both the atrial sense and ventricular sense signals are inputted into the atrial capture detection block 75, as shown.

Decision block 72 determines whether an atrial stimulus should be delivered. A decision to deliver an atrial stimulus, e.g., an ASP, is connected to block 74, and the pacemaker provides an atrial output. An $A_{13}$ stim indication of a delivered atrial stimulus is inputted into atrial capture detection block 75.

In addition to the A_stim signal and the atrial and ventricular sense signals, capture detection block 75 also receives inputs from other modules 78, such as impedance or activity. The evoked P-wave module 76 looks for an evoked P-wave following delivery of an atrial pace pulse. Thus, module 76 attempts to determine capture directly by looking for the evoked response signal; this may be reliable in a DDD pacing system, but generally is not available for a VDD system. Due to the unreliability of direct evoked P-wave detection, there is a need to confirm from another source or sources. If the evoked P-wave detection proves reliable, its contribution can be increased in the weigh module 80, discussed below. The timing module 77 looks at timing sequences and rate, as discussed at length below. Within timing module 77, a set of logic rules are stored which characterize the timing features of the module. Some of the rules are more important than others, and accordingly indicate a greater probability, as illustrated below. Thus, after processing each of the rules, there results a certain probability of capture, no$_{13}$ capture. Module 79, designated "other" looks at any other information which may be programmed into the pacemaker for determining a probability of atrial capture. The result of all three modules, if all are operating, contributes to the probability that the atrial stimulus resulted in capture, no_capture, or maybe_capture.

The outputs are compared by weight module 80, producing a decision of capture, no_capture, or may_be_capture, which decision is connected to diagnostics block 81 and evaluation block 82. A feedback loop from block 81 goes back to atrial sense interpretation block 70, to indicate whether the last A_pace should be accepted or ignored. As discussed further in connection with FIG. 8 below, the result of the evaluation at block 82 is to adjust the atrial output, i.e., increase or decrease it, and/or to send an enable or disable signal to decision block 72.

Figure 5:
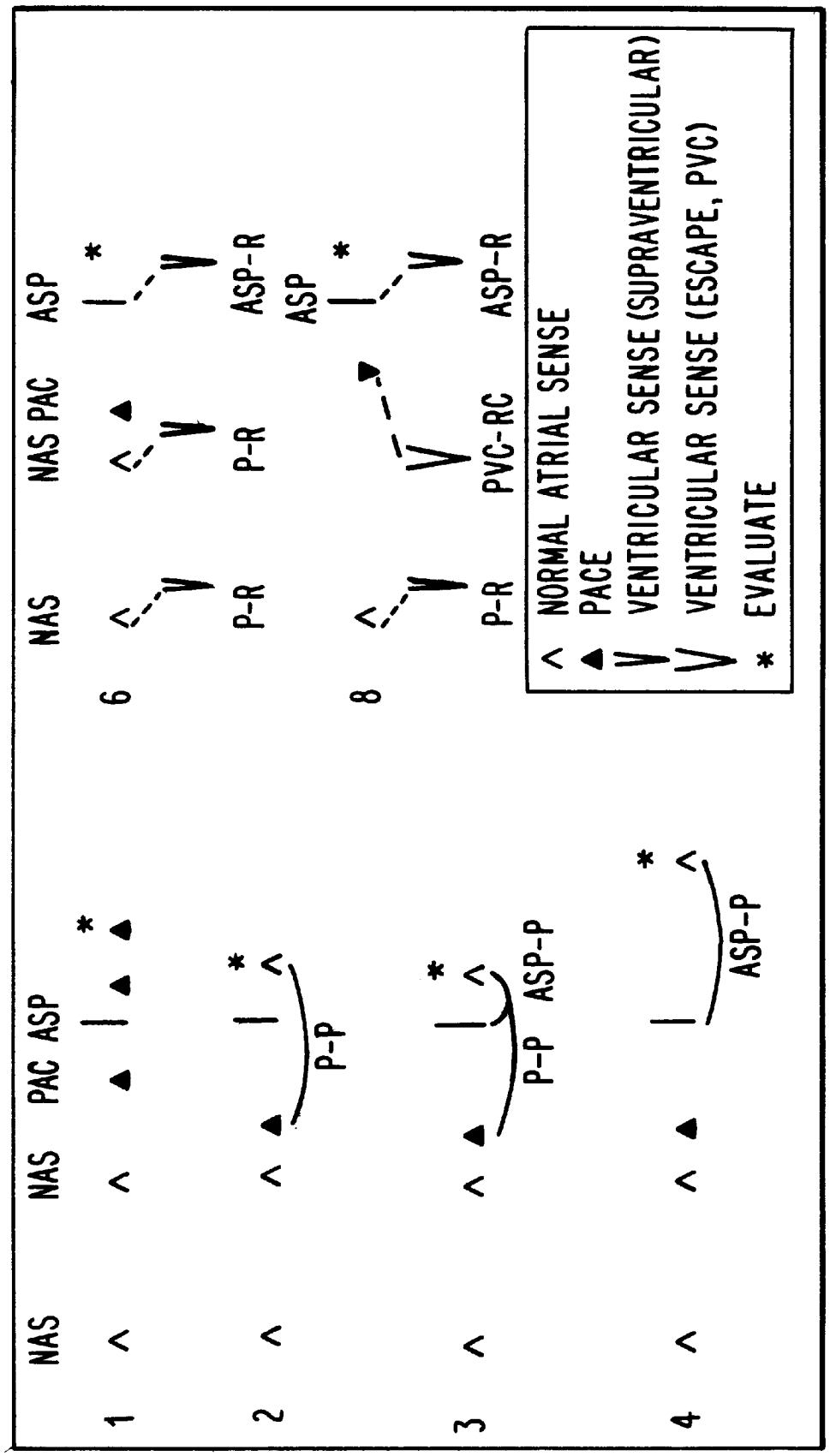
FIG. 5 presents a series of timing diagrams illustrating respective exemplary rules for determining probability of atrial capture or no capture in different specific situations.

Timing module 77 contains algorithms for checking a plurality of rules which are used to determine the likelihood of atrial capture following an ASP. Generally. such rules define relationships involving atrial intervals (A—A) and atrial to ventricular intervals (AS–VS). Referring to FIG. 5, there are shown six timing diagrams reflecting six of the rules for determining the likely result of a delivered ASP. The counters used in following these rules are as follows:

the capture counter, T_capt the no_capture counter, T$_{no}$_capt the may_be_capture counter, T_may_be_capt The rules illustrated here are illustrative of programmable rules for determining the probability that an ASP has or has not resulted in atrial capture. While these rules illustrate evaluating an ASP, the principles can be extended to continuous atrial pacing; while the invention has primary application to atrial pacing with floating electrodes, it can also be utilized in any other situation where evoked P-wave sensing is not reliable, e.g., a dislodgement of the atrial lead. As seen in the following discussion, evaluation of all of the rules results in a certain probability that the ASP resulted in capture, reflected by the capture counter T_capt; a certain probability did not result in capture, reflected by the no_capture counter T_no_capt; and the situations where it may be capture, reflected by the T_may_be_capt counter. The rules are formulated to apply to specific sequences of events and rates related to delivery of an ASP, where a sequence may include events before and after, or just after delivery of an ASP.

A pacemaker can be programmed to react to a sensed PAC by trying to deliver an ASP, as discussed above. The important timing features of PACs that are relevant here are that they can be normally conducted, causing ventricular contraction at either a normal PQ interval or a delayed interval. The additional intra-atrial delay following a PAC is usually about 50–60 ms, although on rare occasions this is no delay if the sinus node is not reset. Thus, the PAC_P interval is usually just slightly longer than the dominant sinus cycle, but less than compensatory. Sometimes it is exactly the same; and sometimes it is fully compensatory or even longer if the sinus cycle is totally suppressed. Based on these characteristics of PACs, the following six rules apply for evaluating an ASP on PAC:

| 1 | IF (#P > 1 in previous cycle) | THEN ignore evaluation this cycle |
|---|---|---|
| 2 | IF \|P_P-Avr_Atrial_int\| < 1/8 Avr_Atrial_int | THEN T_no-capt + 1 |
| 3 | IF (ASP_P < 250 msec) | THEN T_no_capt + 5 |

-continued

| 4 | IF (ASP_P > 7/8 Avr_Atrial_int) | THEN T_capt + 1 |
|---|---|---|
| 5 | IF (P_P = 2*Avr_Atrial_int) | THEN T_may_be_capture + 1 |
| 6 | IF (P_R$_{pre\_PAC}$ AND PAC AND ASP_R | THEN T_capt + 5 |

Rules 1–4 and 6 are illustrated in FIG. 5. With respect to Rule 1, the plural number of P senses indicate that an arrhythmia has started and no clear observation is possible. Consequently, no evaluation is made this cycle based on timing. Rule No. 2 is based on the premise that a P_P interval would normally have up to a 12.5% variation. Consequently, if a P_P interval around an ASP is a variation which is less than 12.5%, this indicates that the ASP did not capture and cause the next P sense, and consequently the T_no_capt counter is incremented by 1. With regard to Rule 3, it is noted that cardiac intervals are longer than 250 ms, except in cases of flutter and fibrillation. Consequently, if the ASP_P interval is less than 250 ms, this raises a strong suggestion that the ASP did not capture, and the T_no_capt counter is suitably incremented with extra weight, e.g., by 5 counts. Looking at Rule 4, it is noted that when an ASP is delivered, it is delivered before the next sinus is expected, and thus at an interval shorter than the dominant sinus interval. If the sino-atrial node is reset by the ASP, then the next sinus beat is to be expected at a regular or somewhat extended interval. Consequently, if the ASP_P interval is more than ⅞, the average atrial interval, this suggests capture and the T_capt counter is incremented.

Rule 5, not illustrated illustrated in FIG. 5, is simply that if the P_P interval surrounding an ASP is about twice the average atrial interval, then capture may be indicated, and the T$_{may}$_be_capt is incremented. Although the ASP_P interval seems to be long enough that capture is most likely, it could also be that there has been a sinus beat in between which occurred during the ASP or a ventricular pace, and was blanked. Thus, in this situation, the ASP may or may not have been effective.

With respect to Rule 6, if the P wave preceding the PAC is normally conducted, and the ASP is conducted to result in a V sense, this strongly suggests atrial capture by the ASP. In this situation, the P_capt counter is incremented by a heavily weighted factor, e.g., 5.

The timing features of PVCs are important for devising what rules are applicable for determining whether an ASP delivered in response to a PVC has captured the atrium. Most PVCs do not disturb the sinus rhythm, and are therefore followed by a compensatory pause; but is quite common for the ectopic impulse to be conducted retrogradely into the atria, usually 120–200 ms after the beginning of the ventricular beat. Consequently, most of the rules as defined for an ASP on PAC are also applicable for an atrial pace pulse delivered just after the PVC is recognized, except Rule 6. An additional rule is based on the fact that PVCs may be retrogradely conducted (RC into the atria):

7. IF (RC is possible AND VA is approximately VARC), THEN T_no_capt+5.

Note that the evidence that retrograde conduction exists, and the observed VA intervals during RC, are determined based on atrial and ventricular timing, in block 77.

For an ASP after PVC, again Rules 1–5 are applicable; Rule 7 is still applicable. In addition, an additional rule designated as Rule 8 is focused on the fact that both anterograde and retrograde paths exist, as illustrated timing diagram 8 of FIG. 5:

8. IF (P_R$_{pre\_pvc}$ AND PVC_RC AND ASP_R) THEN T_capt+5.

Note that where a P-wave preceding a PVC is normally conducted and is also conducted following the ASP, then this strongly suggests atrial capture by the ASP, and the T_capt counter is incremented strongly, e.g., by 5.

As discussed above, RC may be a reason for delivering an ASP. It is noted that a retrograde conducted atrial contraction may be of nodal or ventricular origin, as from a PVC. Consistent retrograde conduction may be seen during ventricular tachycardia (VT) as well as following ventricular pacemaker stimulation. Consistent retrograde conduction due to ventricular stimulation usually is characterized by fairly constant VA intervals; occasionally retrograde conduction is observed during VT with Wenckebach periodicity or in an N:1 ratio. For an ASP on RC, i.e., ASP delivered to try to terminate RC, only prior rules 1 and 3 remain applicable. The following two rules can also be used:

9. IF ($VA_{pre-ASP}$=$VA_{post-ASP}$) THEN T_no_capture+5

10. IF (no P in previous cycle) THEN Tcapt+1

Note that with respect to Rule 9, this condition presents very strong proof that the ASP does not result in capture, since the VA interval was not changed; consequently the T_no_capture counter is incremented heavily. The proposition of Rule 10, i.e., if no P-wave then RC has stopped, suggests that the ASP did result in capture, and the T_capt counter is incremented; note that the intrinsic sinus rhythm is probably lower than the ventricular rhythm.

As used in relation to this invention, the term sequence means a certain arrangement of events and/or rates in relation to the delivered atrial pace pulse. The rules as given above are exemplary, and other such timing rules can be employed within the scope of the invention.

Figure 6A:
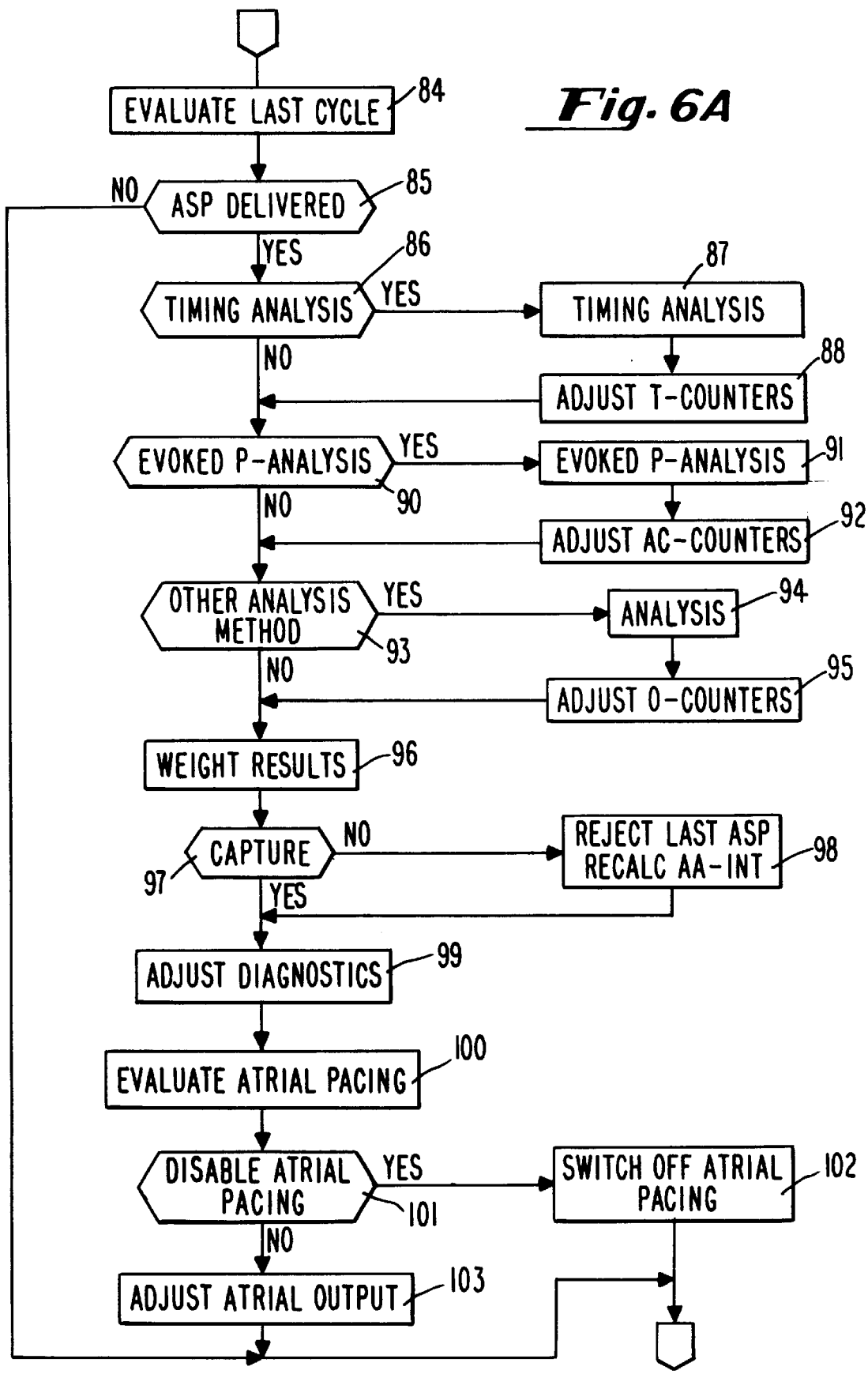
FIG. 6A is a flow diagram indicating the primary steps taken each cycle in accordance with this invention, for obtaining capture efficiency data.

Referring now to FIG. 6A, there is a shown a flow diagram of the primary steps taken each cycle in accordance with this invention. As illustrated at 84, the least cycle is evaluated, meaning that there is an atrial sense interpretation for an AS, a ventricular sense interpretation for a VS, A—A and V—V timing is determined, etc. At 85, it is determined whether an atrial stimulus, an ASP in the preferred embodiment, as been delivered. If No, the routine exits. If Yes, the routine goes to 86, and determines whether the timing analysis of module 77 is to be performed. If Yes, the analysis is done at 87, and each of the timing (T) counters is adjusted at 88 to correspond to the timing analysis. At 90, it is determined whether the evoked P-wave analysis is to be done. If Yes, this analysis is done at 91, and the AC counters are adjusted accordingly at 95. At 93, it is determined whether any other analysis method has been programmed, and is to be performed. If yes, this is done at 94, and the (O) counters are adjusted at 95. At 96, the results are weighed, as discussed in more detail in FIG. 6C. Based on the weighed results, the determination of whether there has been capture is made at 97. If No, then the last ASP is rejected for logic purposes, and the A—A interval is recalculated, as shown at 98. At 99, the diagnostic data is adjusted to account for the last interval. At 100, the pacemaker evaluates atrial pacing, based on efficiency data as discussed in connection with FIGS. 7 and 8. At 101, it is determined whether the evaluation calls for disabling atrial pacing. If Yes, at 102 atrial pacing is switched off; if No, at 103, the atrial pace pulses output is adjusted, to obtain more efficient performance.

Figure 6B:
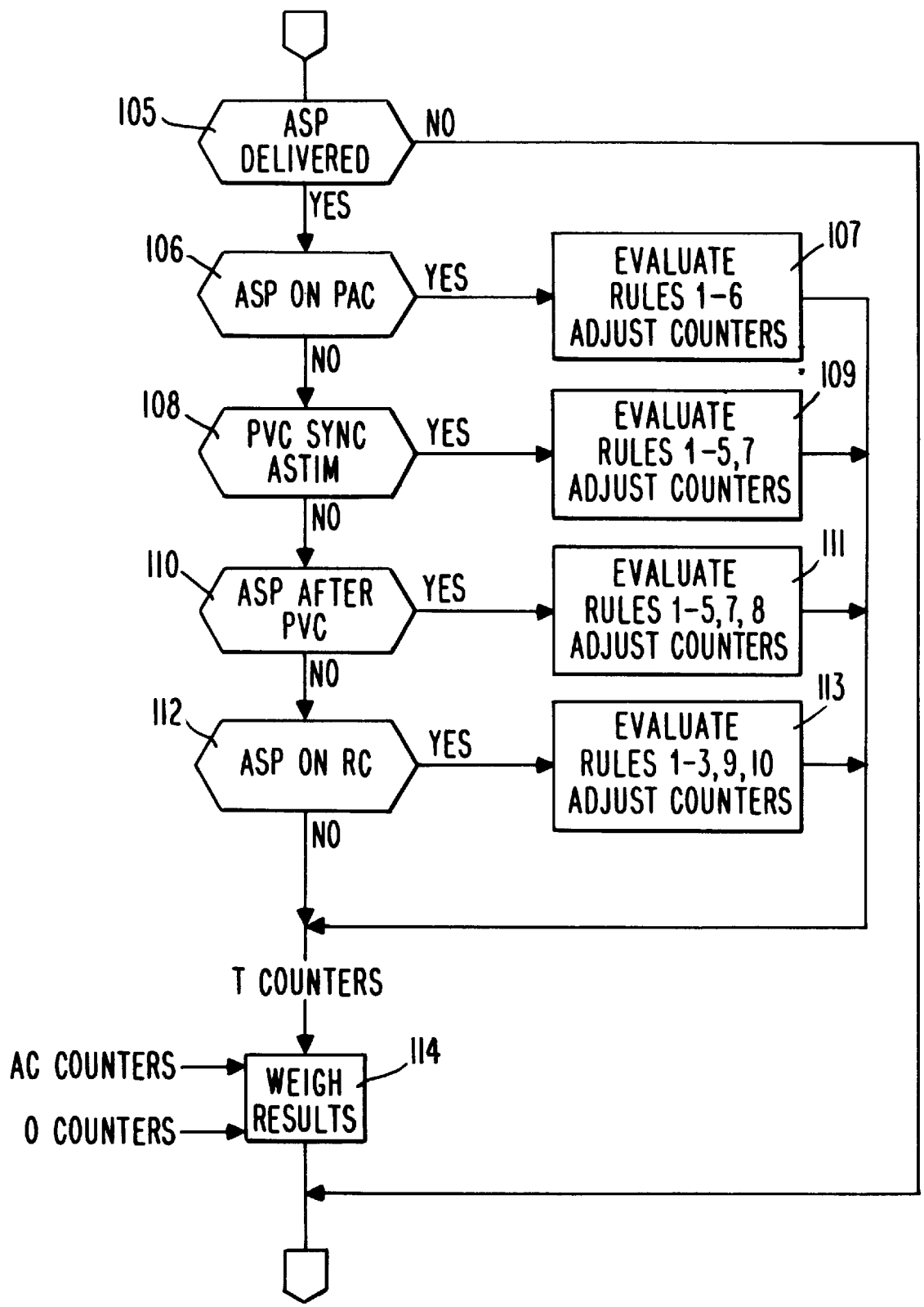
FIG. 6B is a more detailed flow diagram illustrating the steps taken in the timing module used for determining probability of atrial capture due to a delivered atrial pace pulse, as well as the weighing module for weighing atrial capture data.

Referring now to FIG. 6B, there is shown a more detailed diagram of the operation of the timing module in accordance with the above discussion of rules 1–10. At 105, it is determined whether an ASP, or other atrial pace pulse has been delivered. If No, the routine of FIG. 6B is exited. If Yes, at 106 it is determined whether there has been an ASP on PAC. If Yes, at 107 rules 1–6 are evaluated, and the appropriate counters are adjusted. If the answer at 106 is No, at 108 it is determined whether there as been a PVC synchronous Astim, and if Yes, rules 1–5 and 7 are evaluated, and the appropriate counters are adjusted. If the answer at 108 is No, at 110 it is determined whether there as been an ASP after PVC. If Yes, at 111 rules 1–5, 7 and 8 are evaluated, and the appropriate counters are adjusted. If the answer at 110 is No, at 112 it is determined whether there has been an ASP on RC. If Yes, at 113 rules 1–3, 9 and 10 are evaluated, and the appropriate counters are adjusted. Following any evaluation of an ASP or other Astim, the data from the timing (t) counters is weighed, along with the AC and O counters, to provide the capture determination, as shown in FIG. 6C.

Figure 6C:
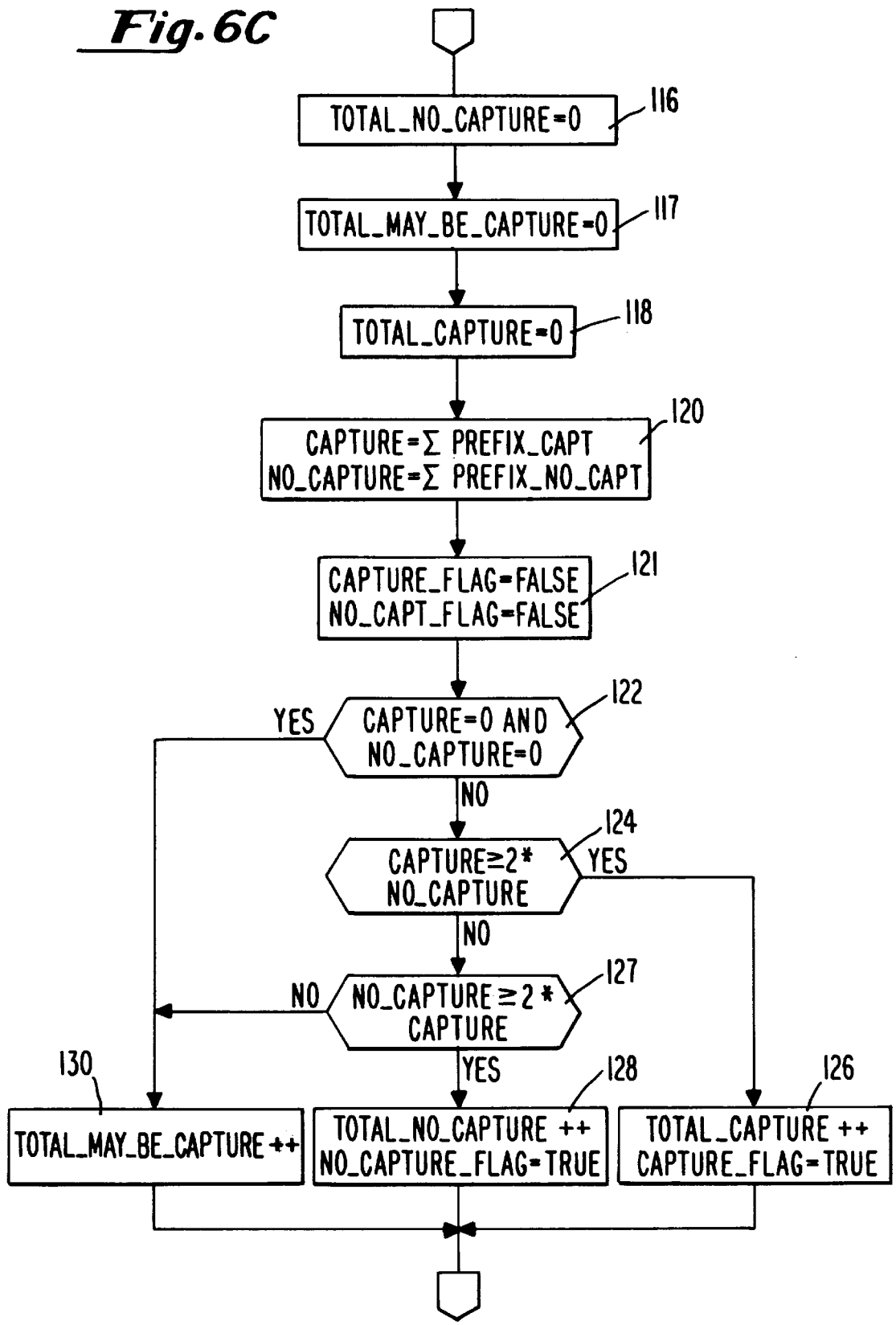
FIG. 6C is a flow diagram of the weigh module shown in FIG. 4.

Referring now to FIG. 6C, there is shown a flow diagram of the weigh module illustrated at 80 in FIG. 4. This module carries out the logic for taking the counter outputs from each of the modules 76, 77, and 79, and making therefrom a final decision as to whether the atrial pace did or did not result in capture, or maybe resulted in capture. It is to be emphasized that this flow diagram is illustrative and other schemes for weighing the module outputs can be used in the scope of this invention. As used in FIG. 6C, "prefix" refers to the module prefix, i.e., T for Timing; AC for auto-capture or evoke P-wave detection; and O for other. At blocks 116, 117 and 117, the total_no_capture, total_may_be_capture, and total_capture counters respectively are initialized to zero.

At block 120, the capture count is set equal to the sum of prefix_capt, or the sum of the different module capture counters. Likewise, the no_capture count is set equal to the sum of the no_capture counters. At 121, both the capture_flag and the no_capt_flag are set FALSE. At 122, it is determined whether capture=0 AND no_capture=0. If yes, this means that there has been no indication one way or the other, and the routine branches to 130 and increments the total_may_be_capture counter by 1. If at 122, the answer is no, the routine goes to 124 and determines whether the capture counter is equal to or greater than 2 times the value of the no_capture_counter. If yes, this strongly indicates capture, and the routine branches to 126 and increments the total_capture counter by 1 and sets the capt_flag equal to TRUE. If, at 124, the answer is no, the routine goes to 127 and determines whether the count in the no_capture counter is equal or greater than 2 times the count in the capture counter. If yes, this strongly indicates no_capture, and the routine goes to 128 where the total_no_capture counter is incremented by 1, and the no_capt_flag is set TRUE. If the answer at 127 is no, the situation remains ambiguous, and so the routine branches to 130 and increments the total_may_be_capture counter by 1. Thus, each time an atrial pace pulse is delivered, the probability evaluation is made and the pulse is classified in one of three ways, and a count is maintained of the distribution of pace pulses between the three possibilities of capture, no_capture and may_be_capture. The accumulated counts in the respective counters provide a measure of the ongoing atrial pace capture efficiency.

Figure 7:
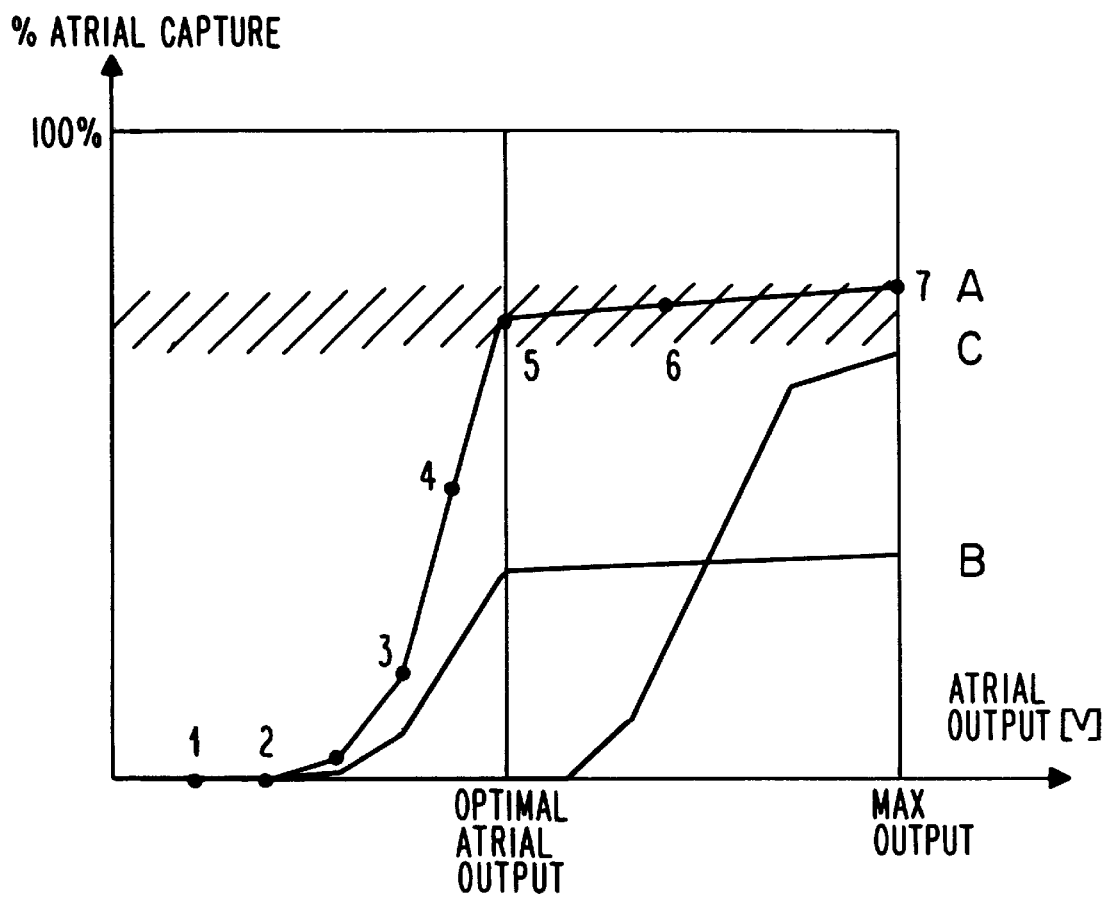
FIG. 7 is a graph showing the relationship between atrial output level and percent of atrial capture.

Referring now to FIG. 7, there is shown a graph charting percentage atrial capture as a function of atrial stimulus output. Referring first to curve A, it is seen that at output settings 1–4, the percentage atrial capture deviates greatly from the percentage capture as measured at the highest pace pulse output (MAX output) which is indicated at point 7. In between, at points 5 and 6, the deviation is relatively small, and acceptable. Referencing percentage atrial capture to the capture at MAX output, point 7, it is seen that the output level can be dropped down to the level corresponding to point 5, without any significant decrease in efficiency. However, for lower output levels, the efficiency decreases rapidly. Accordingly, the knee of the curve indicates the optimal atrial output. in the sense that output levels below the knee produce an unacceptably low percentage atrial capture, while higher output levels do not achieve any significantly higher percentage capture, but cost significantly more power expenditure. Curve B illustrates another single pass lead situation where the percentage capture is unacceptably low, all the way up to maximum output. In this situation, it is presumed that the floating atrial electrodes simply are not in position for efficient stimulation of the atrium; cessation of atrial pacing is likely indicated, and is an available option. With respect to curve C, a capture percentage close to that of the acceptable range for curve A is achieved only at maximum output power, which would probably be unacceptable for most conditions. In this case, it could be decided to limit atrial pace pulses to ASPs and disable continuous on-demand atrial pacing.

With the data of FIG. 7 in mind, it remains to provide a reliable evaluation of atrial pacing efficiency. As used herein, efficiency is defined in terms of percentage capture over a number of pulses, not merely a determination of capture or no_capture following a given atrial pace pulse. A possible approach to evaluating atrial pacing would be to do a continuous search at different atrial pace output levels. However, this would mean that many measurements would involve a sub-optimal atrial output, and others would involve outputs at the highest possible level. Thus, such a test would compromise both AV synchrony and energy consumption. On the other hand, for a VDD-type application where atrial pacing is used only to resynchronize, e.g., ASP or back-up-type pacing, a search for the optimal atrial output may take a long time to succeed. Temporary DDD pacing at an increased rate could shorten the time needed for a measurement, but since a number or even all of the atrial stimuli may not be effective, the measurement may become symptomatic due to loss of tracking.

A preferred embodiment of this invention is to organize the measurement of atrial pacing efficiency as a continuous measurement, collecting the data following each delivered atrial stimulus, and making an evaluation only when sufficient data has been collected. Thus, the evaluation may be made after data has been accumulated for n atrial stimulus pulses, where n could be programmed low where only back-up atrial pacing was enabled, but considerably higher where continuous atrial pacing was enabled. The preferred rule for evaluating the atrial output level is that if the percentage capture at the highest atrial output is about the same as or only a little different from the percentage capture at the current atrial output, then the pacemaker decreases atrial output. However, if this is not the case, then atrial output is increased. By this means, the pacemaker tries to stay at the knee of the FIG. 7 curve.

Figure 8:
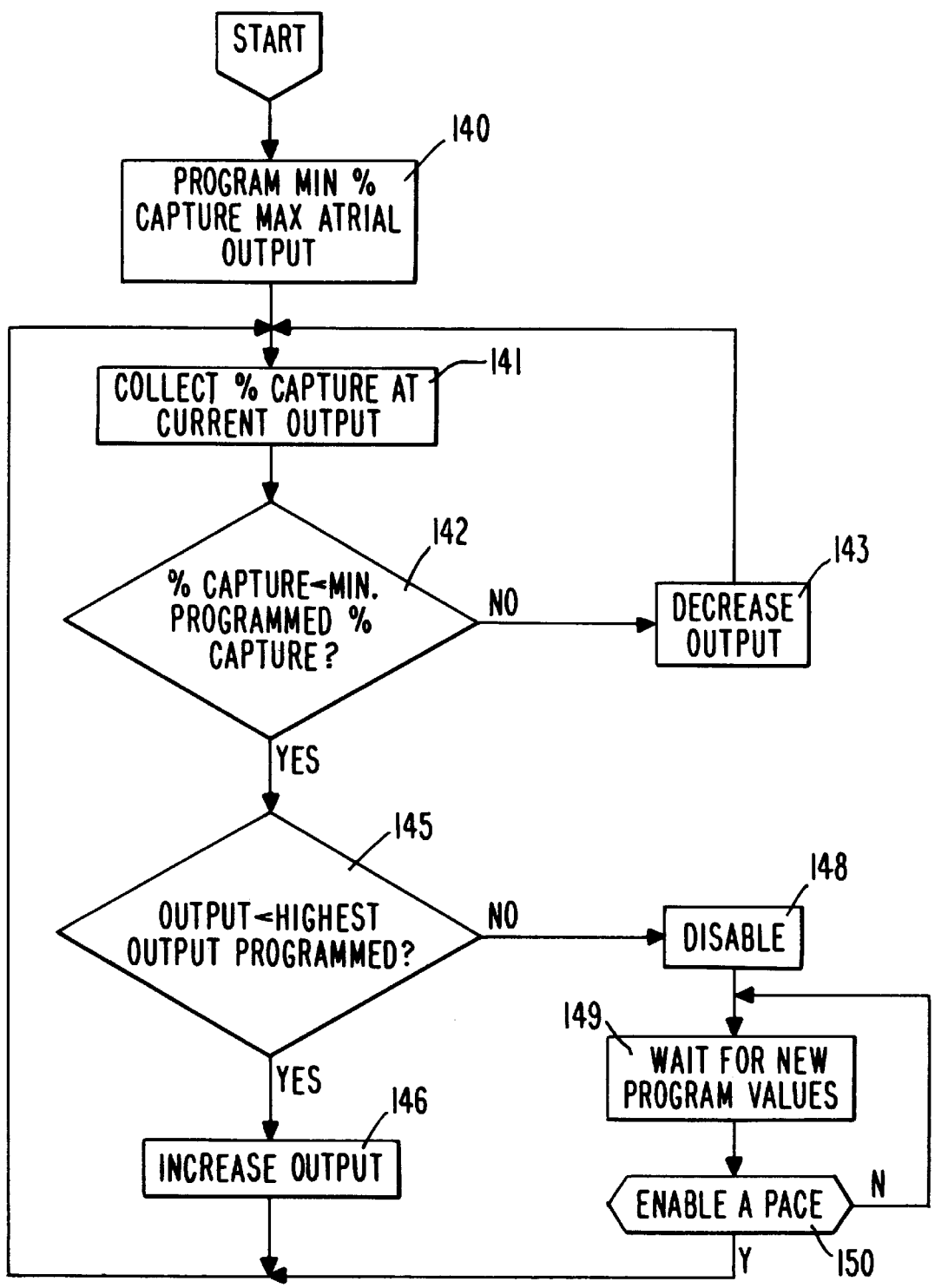
FIG. 8 is a flow diagram illustrating the primary steps taken in evaluating atrial pacing efficiency and adjusting atrial output in accordance with this invention.

FIG. 8 presents a simplified flow diagram of an evaluation routine for determining how and when to change output level. Initially, the minimum percent that is allowable and the maximum atrial output are programmed. The minimum percent capture figure might be determined at the time of implant, or by a subsequent test controlled by external programmer. At 141, data concerning percentage capture at the current output level is collected. After a sufficient amount of data has been collected, at 142 it is determined whether the percentage capture is less than the minimum programmed percentage. If no, meaning that atrial pacing is being done above the optimum knee point, the routine branches to 143 and output is decreased, e.g., by a predetermined change in voltage level or pulse width. However, if the answer is yes, the routine goes to 145 and determines whether the output level is below the highest output program. If yes, then output level can be increased toward the optimal level, and the routine goes to block 146 and increases output. If the answer at 145 is no, meaning that the output is already at the highest output programmed, then atrial pacing is not desired. In this case, the routine goes to 148 and disables atrial pacing. At 149, the pacemaker waits for new program values, in the event that values are externally programmed. When this happens, at 150 it is determined whether atrial pacing can again be enabled. If yes, then the pacemaker goes back to block 141 and starts the collection process.

It is to be noted that other variations of assessing atrial pacing efficiency can be included, which are not illustrated in the drawings. As mentioned, the evaluation of the data may lead to the conclusion that back-up or atrial sync pacing can be accepted, but that the efficiency is not great enough to enable regular pacing, e.g., continuous pacing in the absence of atrial senses.

Although the preferred embodiment uses a single pass lead with floating electrodes, the invention is applicable to other situations where atrial pacing may be problematic, e.g., where the atrial lead is not well fixated, or in cases of poor atrial wall-lead contact. Also, atrial pacing other than ASPs can be evaluated and adjusted.

We claim:

1. A pacing system having a pacemaker adapted for dual mode pacing and a single pass lead for delivering pace pulses to a patient and for sensing patient heartbeat signals, said lead having at least one ventricular electrode positioned for placement in the patient's ventricle and a pair of atrial electrodes positioned to be in the patient's atrium, said pacemaker having ventricular generator means for generating ventricular pace pulses for delivery to said at least one ventricular electrode and atrial pace means for generating atrial pace pulses for delivery to said atrial electrode, and varying means for varying the output level of said atrial pace pulses between a maximum level and a minimum level, comprising:

efficiency means for obtaining a measure of the atrial capture efficiency of said atrial pace pulses at a given output level; and adjusting means for adjusting the atrial pace pulse output level as a function of said capture efficiency measure.

2. The system as described in claim 1, wherein said lead has a pair of floating electrodes positioned to be in the patient's atrium.

3. The pacing system as described in claim 2, comprising control means for enabling said atrial pace means to only generate atrial sync pulses.

4. The pacing system as described in claim 2, wherein said efficiency means comprises max means for determining atrial capture efficiency at said maximum level, and said adjusting means comprises comparing means for comparing atrial capture efficiency at respective different output levels to the said capture efficiency at said maximum level.

5. The pacing system as described in claim 4, wherein said efficiency means comprises means for determining capture efficiency at a current output level and periodic means for periodically determining said maximum level capture efficiency, and said comparing means comprises means for comparing said current and said maximum level efficiencies.

6. The pacing system as described in claim 4, wherein said efficiency means comprises timing means for determining a probability of capture by a delivered atrial pace pulse as a function of the timing of one or more cardiac events occurring in a predetermined sequence which includes said atrial pace pulse.

7. A method of atrial pacing of a patient with a pacemaker system having a single lead with a pair of floating atrial electrodes, comprising pacing the patient's atrium by generating atrial pace pulses at an adjustable output level and delivering said pace pulses through said atrial electrodes, accumulating data representative of the capture efficiency of said pace pulses as a function of output level, and setting the output level of succeeding atrial pace pulses as a function of said data.

8. The method as described in claim 7, comprising periodically adjusting the output level of said atrial pace pulses.

9. The method as described in claim 7, comprising restricting when atrial pace pulses are delivered as a function of said accumulated data.

10. The method as described in claim 9, wherein said restricting comprises restricting delivery of atrial pace pulses to delivery of atrial sync pulses.

11. The method as described in claim 9, wherein said restricting comprises inhibiting DDD pacing.

12. The method as described in claim 7, comprising determining after each delivered atrial pace pulse a probability of capture and a probability of no capture, and wherein said accumulating comprises accumulating each said determined probability.

13. The method as described in claim 12, wherein said determining comprises obtaining timing information of a sequence of cardiac events occurring around each said atrial pace pulse, and determining said probability as a function of said timing information.

14. The method as described in claim 12, wherein said accumulating comprises weighing each determined probability in accordance with a predetermined weighing factor corresponding to respective timing conditions.

15. An implantable cardiac pacemaker system comprising:

atrial generator means for generating atrial pace pulses;

atrial lead means for sensing atrial heartbeats and delivering atrial pace pulses generated by said generator means, said atrial lead means having a pair of electrodes positioned for floating in a patient's atrium;

sequence means for analyzing when events occur in at least one predetermined sequence including a delivered atrial pace pulse;

capture means responsive to said sequence means for accumulating data reflective of when delivered atrial pace pulses resulted in atrial capture; and evaluation means for evaluating atrial pace pulse capture efficiency as a function of said accumulated data.

16. The system as described in claim 15, wherein said sequence means comprises a plurality of stored sequences, each of said sequences representing a respective situation indicating a likelihood of capture, no__capture or may__be__ capture.

17. The system as described in claim 16, comprising control means for controlling the output of generated atrial pace pulses by said atrial generator means, said control means having adjusting means for adjusting the atrial pace pulse output level to an optimal output level which minimizes deviation of capture efficiency from the maximum available capture efficiency while also decreasing output level consistent with said optimal output efficiency.

18. An implanatable cardiac pacemaker system, having atrial generator means for generating and delivering atrial pace pulses, sequence means for obtaining sequence data relating to each delivered atrial pace pulse, and capture means for analyzing said sequence data and making a determination of whether a delivered atrial pace pulse has resulted in capture.

19. The system as described in claim 18, comprising a single pass lead having at least one ventricular electrode for sensing ventricular contractions and a pair of electrodes for sensing atrial contractions.

20. The system as described in claim 18, further comprising ventricular sense means for sensing ventricular heartbeats, and wherein said sequence means comprises timing means for determining A—A timing and AS–VS timing sequences.

21. The system as described in claim 18, wherein said sequence means comprises means for evaluating a plurality of rules relating to events and rates around a said delivered atrial pace pulse.

* * * * *